(12) United States Patent
Zhao et al.

(10) Patent No.: US 7,358,223 B2
(45) Date of Patent: Apr. 15, 2008

(54) BIODEGRADABLE CATIONIC POLYMERS

(75) Inventors: Gang Zhao, Vista, CA (US); Xiaoli Fu, Vista, CA (US); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 273 days.

(21) Appl. No.: 11/216,986

(22) Filed: Aug. 31, 2005

(65) Prior Publication Data

US 2006/0258751 A1    Nov. 16, 2006

Related U.S. Application Data

(60) Provisional application No. 60/615,764, filed on Oct. 4, 2004, provisional application No. 60/698,357, filed on Jul. 11, 2005.

(51) Int. Cl.
*A01N 61/00* (2006.01)
*A01N 43/04* (2006.01)
*C08F 10/00* (2006.01)

(52) U.S. Cl. .................... 514/1; 514/44; 525/280; 536/23.1; 536/24.5; 424/1.45

(58) Field of Classification Search ............. None
See application file for complete search history.

(56) References Cited

U.S. PATENT DOCUMENTS

| | | |
|---|---|---|
| 5,374,681 A | 12/1994 | Kroner et al. |
| 5,811,510 A | 9/1998 | Papisov et al. |
| 5,863,990 A | 1/1999 | Papisov et al. |
| 5,958,398 A | 9/1999 | Papisov et al. |
| 6,159,591 A | 12/2000 | Beihoffer et al. |
| 6,569,528 B2 | 5/2003 | Nam et al. |
| 6,652,886 B2 | 11/2003 | Ahn et al. |
| 6,696,038 B1 | 2/2004 | Mahato et al. |
| 6,878,374 B2 | 4/2005 | Yu et al. |
| 2002/0082362 A1 | 6/2002 | Bracchini et al. |
| 2002/0131951 A1 | 9/2002 | Langer et al. |
| 2003/0120355 A1 | 6/2003 | Hateli et al. |
| 2003/0186916 A1 | 10/2003 | Yu et al. |
| 2003/0215395 A1 | 11/2003 | Yu et al. |
| 2004/0071654 A1 | 4/2004 | Anderson et al. |
| 2004/0166089 A1 | 8/2004 | Yu et al. |
| 2005/0037401 A1 | 2/2005 | Cammack et al. |
| 2005/0049387 A1 | 3/2005 | Van et al. |
| 2005/0080033 A1 | 4/2005 | Van et al. |
| 2005/0089503 A1 | 4/2005 | Li et al. |

FOREIGN PATENT DOCUMENTS

| | | | |
|---|---|---|---|
| EP | 1 279 682 A1 | * | 1/2002 |
| EP | 1 279 682 A | | 1/2003 |
| WO | WO 97/45069 | | 12/1997 |
| WO | WO 02/22174 A1 | | 3/2002 |

OTHER PUBLICATIONS

U.S. Appl. No. 11/134,820, filed May 19, 2005.
U.S. Appl. No. 11/126,878, filed May 10, 2005.
Verma I.M and Somia N., "Gene therapy—promises, problems, and prospects," Nature 389 (1997), pp. 239-242; Marhsall E. Science 286 (2000), pp. 2244-2245.
Boussif O., Lezoualc'h F., Zanta M. A., Mergny M. D., Scherman D., Demeneix B., Behr J. P., "A versatile vector for gene and oligonucleotide transfer into cells in culture and in vivo: Polyethylenimine," Proc Natl Acad Sci USA. Aug. 1, 1995, 92(16) 7297-7301.
Eichman J. D., Bielinska A. U., Kukowska-Latallo J. F., Baker J. R. Jr., "The use of PAMAM dendrimers in the efficient transfer of genetic material into cells," Pharm. Sci. Technol. Today Jul. 2000; 3(7):232-245.
Lim Y. B., Kim S. M., Lee Y., Lee W. K., Yang T. G., Lee M. J., Suh H., Park J. S., "Cationic Hyperbranched Poly(amino ester): A Novel Class of DNA Condensing Molecule with Cationic Surface, Biodegradable Three-Dimensional Structure, and Tertiary Amine Groups in the Interior," J. Am. Chem. Soc., 123 (10), 2460-2461, 2001.
Gosselin, Michael A., Guo, Menjin, and Lee, Robert J. "Efficient Gene Transfer Using Reversibly Cross-Linked Low Molecular Weight Polyethylenimine," Bioconjugate Chem. 2001. 12:989-994.
Lynn, David A.; Anderson, Daniel G.; Putnam, David; and Langer, Robert. "Accelerated Discovery of Synthetic Transfection Ventors: Parallel Synthesis and Screening of a Degradable Polymer Library," J. Am. Chem. Soc. 2001, 123, 8155-8156.
Gottschalk, et al. "Folate receptor mediated DNA delivery into tumor cells: potosomal disruption results in enhanced gene expression," (1994) Gene Ther 1:185-191.
Cotten, et al. "High-efficiency receptor-mediated delivery of small and large (48 Kilobase gene constructs using the endosome-disruption activity of defective of chemically inactivated adenovirus particles," (Jul. 1992) Proc. Natl. Acad. Sci. USA vol. 89: pp. 6094-6098.
Wagner, et al. "Transferrin-polycation conjugates as carriers for DNA uptake into cells," (1990) Proc Natl Acad Sci USA vol. 87: 3410-3414.
Uherek, et al., "A Modular DNA Carrier Protein Based on the Structure of Diphtheria Toxin Mediates Target Call-specific Gene Delivery," (1998) J Biol. Chem. vol. 273:8835-8841.
Vijay Sharma, PhD, Gary D. Luker, MD, and David Piwnica-Worms, MD, Ph.D., "Molecular Imaging of Gene Expression and Protein Function In Vivo With PET and SPECT," Journal of Magnetic Resonance Imaging 16:336-351 (2002).
Zhou et al., Preparation of Poly($_L$-serine ester): A Structural Analogue of Conventional Poly($_L$-serine ester), Macromolecules, 23, 3399-3406 (1990).
Kwon et al., Pseudopoly(amino acids): A Study of the Syntheses and Characterization of Poly(trans-4-hydroxy-N-acyl$_L$-proline esters), Macromolecules, 22, 3250-3255 (1989).

(Continued)

*Primary Examiner*—Richard Schnizer
(74) *Attorney, Agent, or Firm*—Knobbe Martens Olson & Bear LLP

(57) ABSTRACT

Polymers comprising a polyethylenimine, a biodegradable group, and a relatively hydrophobic group are useful for the delivery of bioactive agents to cells.

35 Claims, 9 Drawing Sheets

OTHER PUBLICATIONS

Putnam et al., "Poly(4-hydroxy-$_L$-proline ester): Low-Temperature Polycondensation and Plasmid DNA Complexation," Macromolecules, 32, 3658-3662 (1999).

Lim et al., A Self-Destroying Polycationic Polymer: Biodegradable Poly(4-hydroxy-$_L$-proline ester), J. Am. Chem. Soc. 121, 5633-5639 (1999).

Barrera et al., Synthesis and RGD Peptide Modification of a New Biodegradable Copolymer: Poly(lactic acid-co-lysine), J. Am. Chem. Soc. 115, 11010-11011 (1993).

Akinc et al., "Parallel Synthesis and Biophysical Characterization of a Degradable Polymer Library for Gene Delivery," J. Am. Chem. Soc. 125, 5316-5323 (2003).

International Search Report for PCT application No. PCT/US2005/033274, mailed on Mar. 22, 2006.

Written Opinion for PCT application No. PCT/US2005/033274, mailed on Mar. 22, 2006.

* cited by examiner

DNA binding affinity

7A             Lipofectamine 2000

Typical GFP signal of 293 cells after transfection by 7A and lipofectamine 2000

Luciferase activity in luc 705 cell after antisense oligo delivery by polymer 7A and by lipofectamine 2000

Luciferase activity in CHO-AA8 luc after polymer 7A and lipofectamine 2000 mediated SiRNA delivery Cell survival fraction after transfection using 7A and lipofectamine.

GFP transfection efficiency of 7A after incubation in opti MEM for various periods of time

BIODEGRADABLE CATIONIC POLYMERS

RELATED APPLICATIONS

This application claims priority to U.S. Provisional Application No. 60/615,764, filed Oct. 4, 2004 and U.S. Provisional Application No. 60/698,357, filed Jul. 11, 2005, both of which are hereby incorporated by reference in their entireties.

BACKGROUND OF THE INVENTION

1. Field of the Invention

This invention relates to compositions and methods for delivering bioactive agents to cells. In preferred embodiments, this invention relates to cationic lipopolymers comprising a polyethylenimine (PEI), a biodegradable group, and a relatively hydrophobic group, and to methods of using such lipopolymers to deliver bioactive agents such as DNA, RNA, oligonucleotides, proteins, peptides, and drugs.

2. Description of the Related Art

A number of techniques are available for delivering bioactive agents to cells, including the use of viral transfection systems and non-viral transfection systems. Viral systems typically have higher transfection efficiency than non-viral systems, but there have been questions regarding the safety of viral systems. See Verma I. M and Somia N., Nature 389 (1997), pp. 239-242; Marhsall E. Science 286 (2000), pp. 2244-2245. In addition, viral vector preparation tends to be a complicated and expensive process. Although non-viral transfection systems generally are less efficient than viral systems, they have received significant attention because they are generally believed to be safer and easier to prepare than viral systems.

A number of non-viral transfection systems involve the use of cationic polymers that are complexed to bioactive agents. Examples of cationic polymer that have been used as gene carriers include poly(L-lysine) (PLL), polyethyleneimine (PEI), chitosan, PAMAM dendrimers, and poly(2-dimethylamino)ethyl methacrylate (pDMAEMA). Unfortunately, transfection efficiency is typically poor with PLL, and high molecular weight PLL has shown significant toxicity to cells. In some cases PEI provides efficient gene transfer without the need for endosomolytic or targeting agents. See Boussif O., Lezoualc'h F., Zanta M. A., Mergny M. D., Scherman D., Demeneix B., Behr J. P., Proc Natl Acad Sci USA. Aug. 1, 1995, 92(16) 7297-301. A range of polyamidoamine dendrimers have been studied as gene-delivery systems. See Eichman J. D., Bielinska A. U., Kukowska-Latallo J. F., Baker J. R. Jr., Pharm. Sci. Technol. Today 2000 July; 3(7):232-245. Unfortunately, both PEI and dendrimers have been reported to be toxic to cells, thus limiting the potential for using PEI as a gene delivery tool in applications to human patients. In addition, the cost of polyamidoamine dendrimers having commercially practical gene transfection efficiencies is relatively high.

Gene carriers made with degradable cationic polymers have been reported to transfer genes into mammalian cells with decreased cytotoxicity. See Lim Y. B., Kim S. M., Lee Y., Lee W. K., Yang T. G., Lee M. J., Suh H., Park J. S., J. Am. Chem. Soc., 123 (10), 2460-2461, 2001. Unfortunately, these degradable systems also exhibited lower gene transfer efficiency compared to non-degradable polymers. To improve the transfection efficiency of low molecular weight PEI, Gosselin et al. reported that higher molecular weight PEI could be obtained by using disulfide-containing linkers. See Gosselin, Micheal A., Guo, Menjin, and Lee, Robert J. Bioconjugate Chem. 2001. 12:232-245. PEI polymers made using dithiobis(succinimidylpropionate) (DSP) and dimethyl-3,3'-dithiobispropionimidate-2HCl (DTBP) showed comparable gene transfection efficiency and lower cytotoxicity. However, the disulfide-containing linkers are expensive, which makes large-scale preparation of this system difficult and undesirable. The polymers with disulfide-containing linkers are only degraded under reducing conditions, which limits polymer applications in other conditions.

Lynn, et al. have described a method of synthesizing biodegradable cationic polymers using diacrylates as linker molecules between cationic compounds. See Lynn, David A.; Anderson, Daniel G.; Putnam, David; and Langer, Robert. J. Am. Chem. Soc. 2001, 123, 8155-8156. However, the resulting polymers do not complex well with many bioactive agents. Synthesis of these polymers requires days to complete and the amount of effective product, which can be used in gene delivery, is low. More than one hundred cationic polymers were produced according to the methods of Lynn et al., but only two of these polymers showed effective gene transfection efficiency. These factors make the preparation of high molecular weight polymers by this method difficult to achieve.

Thus, there remains a need for cationic polymers that may be used to safely and efficiently facilitate the delivery of bioactive agents to cells.

SUMMARY OF THE INVENTION

An embodiment provides a polymer comprising a recurring unit selected from the group consisting of formula (Ia) and formula (Ib):

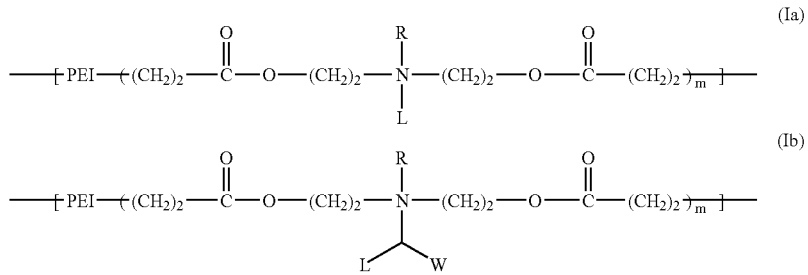

wherein: PEI is a polyethyleneimine recurring unit; R is selected from the group consisting of electron pair, hydrogen, $C_2$-$C_{10}$ alkyl, $C_2$-$C_{10}$ heteroalkyl, $C_5$-$C_{30}$ aryl, and $C_2$-$C_{30}$ heteroaryl; L is selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{50}$ aryl; $C_2$-$C_{50}$ heteroaryl; $C_2$-$C_{50}$ alkynyl, $C_2$-$C_{50}$ heteroalkynyl, $C_5$-$C_{50}$ aryl; $C_2$-$C_{50}$ heteroaryl; $C_2$-$C_{50}$ carboxyalkenyl, and $C_2$-$C_{50}$ carboxyheteroalkenyl; W is a cationic moiety comprising from about 2 to about 50 carbon atoms; and m is an integer in the range of about 1 to about 30.

A recurring unit selected from the group consisting of formula (Ia) and formula (Ib) may be referred to herein as a recurring unit of the formula (I). Thus, for example, a polymer comprising a recurring unit selected from the group consisting of formula (Ia) and formula (Ib) may be referred to herein as a polymer comprising a recurring unit of the formula (I) or as a polymer of the formula (I). A polymer comprising a recurring unit of the formula (I) may be referred to herein as a cationic lipopolymer.

In preferred embodiments, the PEI in formulae (Ia) and (Ib) is represented by a recurring unit of formula (II)

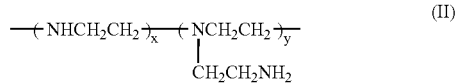
(II)

wherein x is an integer in the range of about 1 to about 100 and y is an integer in the range of about 1 to about 100. Those skilled in the art will appreciate that the nitrogen atom in the recurring unit of formula (I) may bear a cationic charge and thus may form an ionic bond with various negatively charged species, e.g., with an anion such as chloride, bromide, iodide, sulfate, etc. Multiple polymers of the formula (I) may be prepared and stored until use, and thus another embodiment provides a polymer library comprising a plurality of polymers, each of the polymers individually comprising a recurring unit of the formula (I), wherein at least one parameter selected from the group consisting of R, L, PEI, W and m is different for at least two of the polymers.

In another embodiment, the polymer comprising a recurring unit of the formula (I) further comprises a biomolecule that is complexed to the polymer. The biomolecule may bear one or more an anionic groups and may form an ionic bond with the recurring unit of formula (I). Examples of biomolecules bearing one or more anionic groups include nucleic acids (e.g., DNA, single strand RNA, double strand RNA, ribozyme, DNA-RNA hybridizer, siRNA, antisense DNA and antisense oligo), proteins, peptides, lipids, and carbohydrates.

In another embodiment, the polymer comprising a recurring unit of the formula (I) further comprises a biomolecule, a delivery enhancing agent capable of entering a eukaryotic cell, and/or a diagnostic imaging composition that is complexed to the polymer. The delivery enhancing agent may facilitate one or more functions in the eukaryotic cell, e.g., receptor recognition, internalization, escape of the biomolecule from cell endosome, nucleus localization, biomolecule release, and system stabilization.

The polymer comprising a recurring unit of formula (I) which further comprises a biomolecule, and which may further comprise a delivery enhancing agent capable of entering a eukaryotic cell and/or a diagnostic imaging composition that is complexed to the polymer, is useful for transfecting eukaryotic cells. Thus, another embodiment provides a method of transfecting a eukaryotic cell, comprising contacting the cell with such a polymer (comprising a recurring unit of formula (I) and a biomolecule, optionally further comprising a delivery enhancing agent and/or a diagnostic imaging composition) to thereby deliver the biomolecule to the cell. The method may involve treating a mammal, comprising identifying a mammal in need of gene therapy and administering such a polymer to the mammal. In a preferred embodiment, the biomolecule is siRNA, wherein the siRNA is effective to lower expression of a gene of interest.

Another embodiment provides a medical diagnostic system comprising a ligand that recognizes a specific receptor of a eukaryotic cell and a polymer, where the polymer comprises a recurring unit of formula (I) and a biomolecule, and may further comprise a delivery enhancing agent capable of entering a eukaryotic cell and/or a diagnostic imaging composition that is complexed to the polymer.

Another embodiment provides a pharmaceutical composition comprising: a sensitizer agent and a polymer, where the polymer comprises a recurring unit of formula (I) and a biomolecule, and may further comprise a delivery enhancing agent capable of entering a eukaryotic cell and/or a diagnostic imaging composition that is complexed to the polymer. The sensitizer agent may be a compound that undergoes a change in properties on exposure to light or other stimuli, thereby facilitating delivery of the biomolecule (e.g., by increasing the degradation rate of the polymer). The sensitizer agent may itself be a biomolecule that undergoes a change in activity upon stimulus.

These and other embodiments are described in greater detail below.

DETAILED DESCRIPTION OF THE EMBODIMENTS

Figure 1:
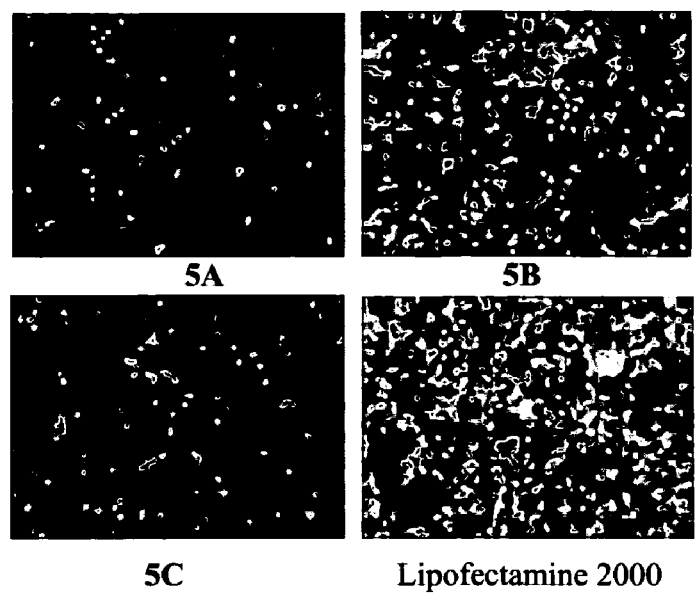
FIG. 1 illustrates typical GFP signals in 293 cells after transfection by lipopolymers (5A, 5B and 5C) and lipofectamine 2000.

An embodiment provides cationic lipopolymers comprising a polyethylenimine, a biodegradable group, and a relatively hydrophobic "lipo" group. Preferred cationic lipopolymers comprise a recurring unit selected from the group consisting of formula (Ia) and formula (Ib):

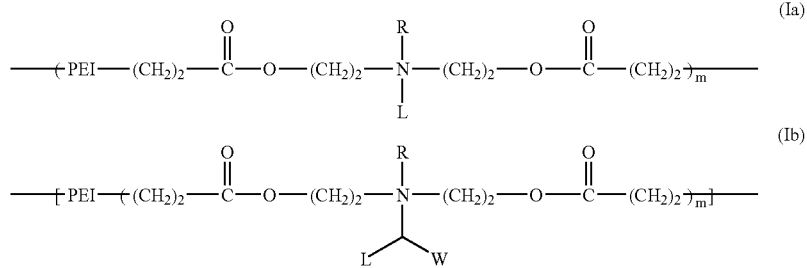

It will be understood that the "formula (I)" as used herein refers to both formula (Ia) and formula (Ib). In formula (I), PEI is polyethyleneimine (e.g., a polymer comprising recurring units represented by the formula (II) above), the ester linkages are biodegradable groups, L represents a relatively hydrophobic "lipo" group, and m is in the range of about 1 to about 30. For example, in certain embodiments L is selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{50}$ aryl; $C_2$-$C_{50}$ heteroaryl; $C_2$-$C_{50}$ alkynyl, $C_2$-$C_{50}$ heteroalkynyl, $C_5$-$C_{50}$ aryl; $C_2$-$C_{50}$ heteroaryl; $C_2$-$C_{50}$ carboxyalkenyl, and $C_2$-$C_{50}$ carboxyheteroalkenyl. In preferred embodiments, L is selected from the group consisting of $C_{12}$ to $C_{18}$ fatty acid, cholesterol, and derivatives thereof. The R in formula (I) may represent an electron pair or a hydrogen atom. Those skilled in the art understand that when R represents an electron pair, the recurring unit of formula (I) is cationic at low pH. The R in formula (I) may also represent a relatively hydrophobic lipo group such as $C_2$-$C_{10}$ alkyl, $C_2$-$C_{10}$ heteroalkyl, $C_5$-$C_{30}$ aryl, or $C_2$-$C_{30}$ heteroaryl, in which case it will be understood that the nitrogen atom bears a cationic charge, generally over a wide pH range.

Cationic lipopolymers comprising a recurring unit of formula (I) may be prepared by reacting a diacrylate monomer of the formula (III) with a polyethyleneimine (PEI) as shown in Scheme A below:

Scheme A

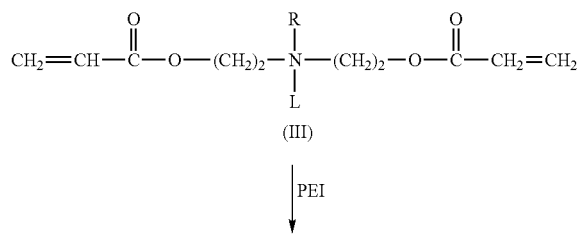

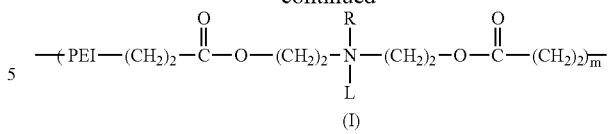

In formula (III), R and L have the same meanings as described above for cationic lipopolymers comprising a recurring unit of formula (I). Scheme A illustrates the preparation of a polymer comprising a recurring unit of the formula (Ia). It will be understood that a polymer comprising a recurring unit of the formula (Ib) may be prepared in a similar manner from the appropriate W group-containing diacrylate monomer. The PEI preferably contains recurring units of the formula (II) in which x is an integer in the range of about 1 to about 100 and y is an integer in the range of about 1 to about 100.

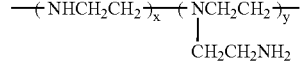

The reaction illustrated in Scheme A may be carried out by intermixing the PEI and the diacrylate (III) in a mutual solvent such as ethanol with stirring, preferably at room temperature for several hours, then evaporating the solvent to recover the resulting polymer. This invention is not bound by theory, but it is believed that the reaction between the PEI and diacrylate (III) involves a Michael reaction between one or more amines of the PEI with double bond(s) of the diacrylate. See J. March, Advanced Organic Chemistry $3^{rd}$ Ed., pp. 711-712 (1985). The diacrylate shown in Scheme A may be prepared in the manner illustrated in the Examples described below.

A wide variety of polymers comprising a recurring unit of the formula (I) may be made in accordance with Scheme A by varying the molecular weight and structure of the PEI, the size and type of the R, W and L groups on the diacrylate (III), and the ratio of diacrylate (III) to PEI. Mixtures of different diacrylates and/or mixtures different PEI's may be used. The PEI may be multifunctional, and thus may be capable of reacting with two or more diacrylates. Crosslinking agents may be used to produce a crosslinked cationic lipopolymer and/or the relative proportions of multifunctional PEI and diacrylate (III) may be adjusted to produce a crosslinked cationic lipopolymer. The molecular weight of the PEI is preferably in the range of about 600 to about 25,000 daltons. The molar ratio of PEI to diacrylate is preferably in the range of about 1:2 to about 1:20. The weight average molecular weight of the cationic lipopolymer may be in the range of about 500 Daltons to about 1,000,000 Daltons preferably in the range of about 2,000

Daltons to about 200,000 Daltons. Molecular weights may be determined by size exclusion chromatography using PEG standards or by agarose gel electrophoresis. In an embodiment, a polymer library is provided by preparing a plurality of cationic lipopolymers in which R, L, W, PEI, and/or m are different for at least two of the polymers.

The cationic lipopolymer is preferably degradable, more preferably biodegradable, e.g., degradable by a mechanism selected from the group consisting of hydrolysis, enzyme cleavage, reduction, photo-cleavage, and sonication. This invention is not limited by theory, but it is believed that degradation of the cationic lipopolymer of formula (I) within the cell proceeds by enzymatic cleavage and/or hydrolysis of the ester linkages.

The cationic lipopolymers may form complexes with biomolecules and thus are useful as carriers for the delivery of biomolecules to cells. Examples of biomolecules that form complexes with cationic lipopolymers of the formula (I) include nucleic acids, proteins, peptides, lipids, and carbohydrates. Examples of nucleic acids include DNA, single strand RNA, double strand RNA, ribozyme, DNA-RNA hybridizer, and antisense DNA, e.g., antisense oligo. A preferred nucleic acid is siRNA. Cationic lipopolymers that comprise a biomolecule that is complexed to the polymer may be formed by intermixing the cationic lipopolymers and biomolecules in a mutual solvent, more preferably by the methods described in the examples below.

Cationic lipopolymers that comprise a biomolecule that is complexed to the polymer may further comprise a delivery enhancing agent capable of entering a eukaryotic cell. The delivery enhancing agent may be dissolved or mixed with the complex, or may be coupled (e.g., covalently bonded or complexed) to the cationic lipopolymer. Delivery enhancers are substances that facilitate transport of a biomolecule into a cell, typically by enhancing transport of a biomolecule/carrier complex across a membrane, reducing degradation during transport, and/or facilitating release of the biomolecule from the carrier. Transport of a biomolecule, such as a gene, into a cell preferably involves releasing the biomolecule from the carrier after the biomolecule/carrier complex has crossed the cell membrane, endosome membrane, and nuclear membrane. For example, in the case of a nucleic acid, the nucleic acid/carrier complex first passes through the cell membrane. When this is accomplished by endocytosis, the nucleic acid/carrier complex is then internalized. The carrier along with the nucleic acid-cargo is enveloped by the cell membrane by the formation of a pocket and the pocket is subsequently pinched off. The result is a cell endosome, which is a large membrane-bound structure enclosing the nucleic acid cargo and the carrier. The nucleic acid-carrier complex then escapes through the endosome membrane into the cytoplasm, avoiding enzyme degradation in the cytoplasm, and crosses the nuclear membrane. Once in the nucleus, the nucleic acid cargo separates from the carrier.

In general, delivery enhancers fall into two categories: viral carrier systems and non-viral carrier systems. Because human viruses have evolved ways to overcome the barriers to transport into the nucleus discussed above, viruses or viral components are useful for transporting nucleic acids into cells. One example of a viral component useful as a delivery enhancer is the hemagglutinin peptide (HA-peptide). This viral peptide facilitates transfer of biomolecules into cells by endosome disruption. At the acidic pH of the endosome, this protein causes release of the biomolecule and carrier into the cytosol. Other examples of viral components useful as delivery enhancers are known to those skilled in the art.

Non-viral delivery enhancers are typically either polymer-based or lipid-based. They are generally polycations which act to balance the negative charge of the nucleic acid. Polycationic polymers have shown significant promise as non-viral gene delivery enhancers due in part to their ability to condense DNA plasmids of unlimited size and to safety concerns with viral vectors. Examples include peptides with regions rich in basic amino acids such as oligo-lysine, oligo-arginine or a combination thereof and PEI. These polycationic polymers are believed to facilitate transport by condensation of DNA. Branched chain versions of polycations such as PEI and starburst dendrimers can mediate both DNA condensation and endosome release. See Boussif, et al. (1995) Proc. Natl. Acad. Sci. USA vol. 92: 7297-7301. PEI can be prepared as a highly branched polymer with terminal amines that are ionizable at pH 6.9 and internal amines that are ionizable at pH 3.9. Because of this organization, PEI can generate a change in vesicle pH that leads to vesicle swelling and, eventually, release from endosome entrapment.

Another way of enhancing delivery is for the cationic lipopolymer to comprise a ligand that is recognized by a receptor on the cell that has been targeted for biomolecule cargo delivery. Biomolecule delivery into the cell may then be initiated by receptor recognition. In this context, the term "ligand" refers to a biomolecule which can bind to a specific receptor protein located on the surface of the target cell or in its nucleus or cytosol. In an embodiment, the ligand may be an antibody, hormone, pheromone, or neurotransmitter, or any biomolecule capable of acting like a ligand, which binds to the receptor. An antibody refers to any protein produced by a B lymphocyte in response to an antigen. When the ligand binds to a particular cell receptor, endocytosis is stimulated. Examples of ligands which have been used with various cell types to enhance biomolecule transport are galactose, transferrin, the glycoprotein asialooorosomucoid, adenovirus fiber, malaria circumsporozite protein, epidermal growth factor, human papilloma virus capsid, fibroblast growth factor and folic acid. In the case of the folate receptor, the bound ligand is internalized through a process termed potocytosis, where the receptor binds the ligand, the surrounding membrane closes off from the cell surface, and the internalized material then passes through the vesicular membrane into the cytoplasm. See Gottschalk, et al. (1994) Gene Ther 1:185-191.

Various delivery enhancing agents are believed to function by endosome disruption. For example, in addition to the HA-protein described above, defective-virus particles have also been used as endosomolytic agents. See Cotten, et al. (July 1992) Proc. Natl. Acad. Sci. USA vol. 89: pages 6094-6098. Non-viral agents are typically either amphiphilic or lipid-based.

The release of biomolecules such as DNA into the cytoplasm of the cell may be enhanced by agents that mediate endosome disruption, decrease degradation, or bypass this process all together. Chloroquine, which raises the endosomal pH, has been used to decrease the degradation of endocytosed material by inhibiting lysosomal hydrolytic enzymes. See Wagner, et al. (1990) Proc Natl Acad Sci USA vol. 87: 3410-3414. Branched chain polycations such as PEI and starburst dendrimers also promote endosome release as discussed above.

Endosomal degradation may be bypassed by incorporating subunits of toxins such as *Diptheria* toxin and *Pseudomonas* exotoxin as components of chimeric proteins that may be incorporated into the cationic lipopolymer/biomolecule complex. See Uherek, et al. (1998) J Biol.

Chem. vol. 273: 8835-8841. These components promote shuttling of the nucleic acid through the endosomal membrane and back through the endoplasmic reticulum.

Once in the cytoplasm, transport of the biomolecule cargo to the nucleus may be enhanced by inclusion of a nuclear localization signal on the nucleic acid-carrier. For example, a specific amino acid sequence that functions as a nuclear-localization signal (NLS) may be used. It is believed that the NLS on a biomolecule/carrier complex interacts with a specific nuclear transport receptor protein located in the cytosol. Once the biomolecule/carrier complex is assembled, the receptor protein in the complex is thought to make multiple contacts with nucleoporins, thereby transporting the complex through a nuclear pore. After the biomolecule/carrier complex reaches its destination, it dissociates, freeing the cargo and other components. The sequence Pro-Lys-Lys-Lys-Arg-Lys-Val (SEQ ID NO.: 1) from the SV40 large T-antigen may be used for transport into nuclei. It is believed that this short sequence from SV40 large T-antigen may provide a signal that causes the transport of associated macromolecules into the nucleus.

The cationic lipopolymer may further comprise a diagnostic imaging compound such as a fluorescent, radioactive, or radio-opaque dye that is complexed to the polymer. The complex may be formed by intermixing the cationic lipopolymer and the diagnostic imaging compound in a mutual solvent. After administration to a mammal, the polymer (complexed with the diagnostic imaging compound) may be tracked using well known techniques such as PET, MRI, CT, SPECT, etc. (see Molecular Imaging of Gene Expression and Protein Function In Vivo With PET and SPECT, Vijay Sharma, PhD, Gary D. Luker, MD, and David Piwnica-Worms, MD, Ph.D., JOURNAL OF MAGNETIC RESONANCE IMAGING 16:336-351 (2002)).

Another embodiment provides a pharmaceutical composition comprising: a sensitizer agent and a polymer, where the polymer comprises a recurring unit of formula (I) and a biomolecule, and may further comprise a delivery enhancing agent capable of entering a eukaryotic cell and/or a diagnostic imaging composition that is complexed to the polymer. The sensitizer agent may be a compound that undergoes a change in properties on exposure to light or other stimuli, thereby facilitating delivery of the biomolecule (e.g., by increasing the degradation rate of the polymer). The sensitizer agent may itself be a biomolecule that undergoes a change in activity upon stimulus. The sensitizer agent may be a light activated drug. Suitable light activated drugs include, but are not limited to, fluorescein, merocyanin, xanthene and its derivatives and the photoreactive pyrrole-derived macrocycles and their derivatives. Suitable photoreactive pyrrole-derived macrocycles include, but are not limited to, naturally occurring or synthetic porphyrins, naturally occurring or synthetic chlorins, naturally occurring or synthetic bacteriochlorins, synthetic isobateriochlorins, phthalocyanines, naphtalocyanines, and expanded pyrrole-based macrocyclic systems such as porphycenes, sapphyrins, and texaphyrins.

EXAMPLE 1

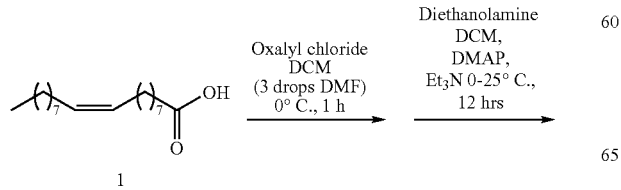

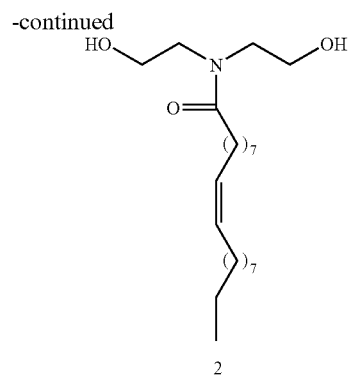

Oxalyl chloride (13.5 mL, 152 mmol) was added to a solution of oleic acid 1 (10.7 g, 38 mmol) in dichloromethane (DCM, 200 mL) and N,N-dimethylformamide (DMF, three drops) at 0° C. The reaction mixture was stirred for about 1 hour and then allowed to warm to room temperature. After 1 hour, the solution was diluted with toluene and distilled. The residue was dissolved in dichloromethane (200 mL) and cooled to 0° C. Diethanolamine (10.9 mL, 114 mmol), 4-(dimethylamino)pyridine (490 mg, 4 mmol), and triethylamine (21 mL, 152 mmol) were added to the solution. The solution was stirred at 0° C. for 30 minutes and then allowed to proceed at room temperature overnight. The reaction mixture was diluted with dichloromethane and washed with 1 N HCl and aqueous $NaHCO_3$. The organic phase was dried ($Na_2SO_4$) and concentrated under reduced pressure. The crude residue was then purified on a silica gel column (10:1 ethyl acetate:methanol), yielding 13.5 g (99.9%) of compound 2 as a colorless oil.

EXAMPLE 2

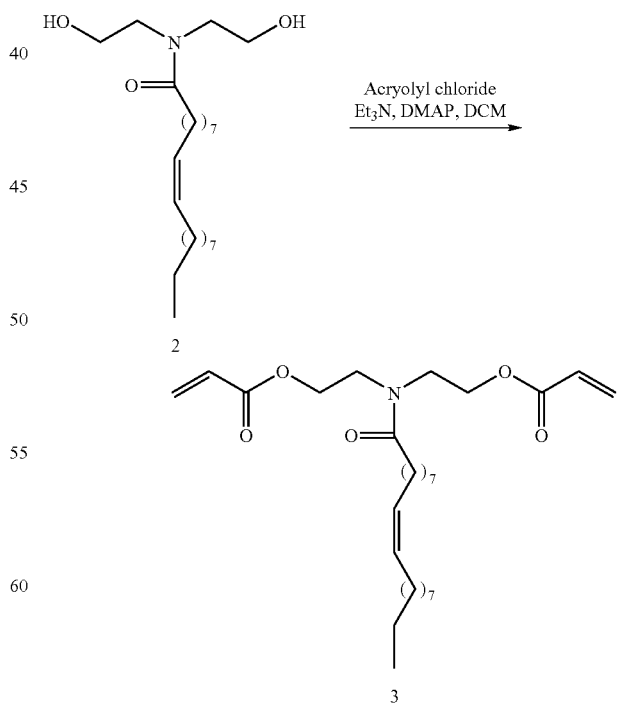

Triethylamine (8.1 g, 80 mmol), DMAP (0.5 g, 4 mmol) and 2 (7.1 g, 20 mmol) was dissolved in 200 ml of dichloromethane at room temperature. The system was flushed with argon and the solution was cooled in an ice bath. Acryolyl chloride (5.4 g, 60 mmol) in 25 ml of dichloromethane was added dropwise. After the addition the reaction was allowed to warm to room temperature and stir overnight. The reaction mixture was diluted with dichloromethane and washed with water and aqueous $NaHCO_3$. The organic phase was dried ($Na_2SO_4$) and concentrated under reduced pressure. The crude residue was then purified on a silica gel column (1:3 ethyl acetate:hexane), yielding 7.5 g (81%) of compound 3 as a colorless oil.

EXAMPLE 3

The synthesis of a cationic lipopolymer was carried out in accordance with Scheme A by reacting polyethylenimine having a molecular weight of 600 (PEI-600) with compound 3 as follows: About 0.6 g of PEI-600 (Aldrich) was weighed and placed in a small vial, and 10 ml of ethanol was added. After the PEI-600 completely dissolved, 3.7 g (8.0 mmol) of 3 in 10 ml of ethanol was added quickly into the PEI solution while stirring. The reaction mixture was stirred for 2 hours at room temperature. After removing the organic solvent under reduced pressure, a transparent, viscous liquid was obtained. $^1$H-NMR spectrum indicated that the acrylic carbon-carbon double bond disappeared completely. The molecular weight of the obtained polymer was estimated by agarose gel electrophoresis. This is a general procedure that serves as a model for other synthetic procedures involving similar compounds, and may be used to synthesize a series of degradable cationic lipopolymers.

EXAMPLE 4

A cationic lipopolymer was prepared as described in Example 3 except that, after stirring the reaction mixture for 2 hours at room temperature (25° C.), the reaction mixture is neutralized by adding 2.5 ml of 4M HCl in ether. The white precipitate 5C is filtered, washed with ethanol, and dried at room temperature under reduced pressure. The obtained polymer 5C was characterized with NMR spectrometer and agarose gel electrophoresis. Polymers 5A and 5B were prepared in a similar manner: 5A: $PEI_{1800}$, m=12; 5B: $PEI_{600}$, m=3; 5C: $PEI_{600}$, m=8. This is a general procedure that serves as a model for other synthetic procedures involving similar compounds, and may be used to synthesize a series of degradable cationic lipopolymers.

EXAMPLE 5

Cell culture: HEK 293T, 208F, HT 1080-EGFP and HeLa-EGFP cells are maintained in DMEM containing 10% FBS, 100 units/ml penicillin and 100 µg/ml streptomycin at 37° C., 5% $CO_2$ and 100% humidity condition. In this media the cells have a doubling time of about 20 hours and were split every 3-4 days to avoid confluency.

EXAMPLE 6

Plasmid DNA preparation: pEGFP-N1 plasmid was purchased from BD Sciences Clontech company, encodes a red-shifted variant of wild-type GFP which has been optimized for brighter fluorescence and higher expression in mammalian cells. The GFP protein was controlled by immediate early promoter of CMV ($P_{CMV\ IE}$). The plasmids were amplified in DH5α E. coli and purified with Qiagen Plasmid Max Preparation Kit, and always had an A260/A280 greater than 1.7.

EXAMPLE 7

In vitro transfection: 293 and 208F cells were plated in 96-well tissue culture plates ($5\times10^4$ cells/well for 293 cells and $1\times10^4$ cells/well for 208F cells) and incubated overnight in DMEM with 10% FBS. The precise mixing order of the plasmid-polymer complex is a critical parameter in the outcome of the transfection. For each well, an aliquot of 7.5 µl lipopolymer solution at different concentration was added into 7.5 µl DNA solution containing 0.6 µg of pEGFP-N1 plasmid and mixed completely. The DNA and lipopolymer mixture were incubated for 15 minutes at room temperature to allow for the formation of DNA-lipopolymer complexes. The complexes were added each well and the cells were incubated at 37° C., 5% $CO_2$ for 24 hours. The EGFP gene transfection efficiency was determined by GFP signal analysis. Lipofectamine were used as positive controls according to the protocol provided by manufacturer.

EXAMPLE 8

Figure 2:
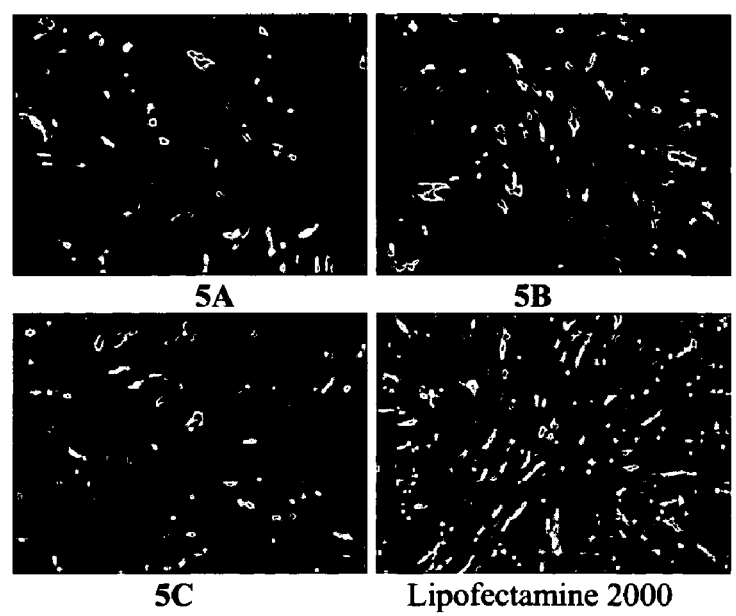
FIG. 2 illustrates typical GFP signals in 208 F cells after transfection by lipopolymers (5A, 5B and 5C) and lipofectamine 2000.

Observation of GFP signal: Green fluorescent signal in transfected cells from Example 3 were observed under fluorescent microscope (Olympus, filter 520 nm). Cells were photographed using a 10× objective. The percent of cells with GFP signal in transfected cultures was determined from counts of three fields for optimal cationic polymer amounts. The transfection efficiency of lipofectamine 2000 was about 60% in 293 cells, efficiency of 5A, 5B and 5C was about 25%, 55% and 40% respectively, but the fluorescent density of 5A and 5C was slightly lower (see FIG. 1). The gene transfection efficiency of above lipopolymers was also detected in 208F, in which the GFP positive cells was about 40%, 45%, 25% and 50% respectively, after transfection mediated by 5A, 5B, 5C and lipofectamine 2000 (see FIG. 2). Although the lipopolymers were not as good as lipofectamine 2000, the transfection efficiency of 5B was very close to lipofectamine 2000, a leading transfection reagent in the market. The results indicated that the lipopolymers have a potential to be transfection reagents for various cells lines.

Figure 3:
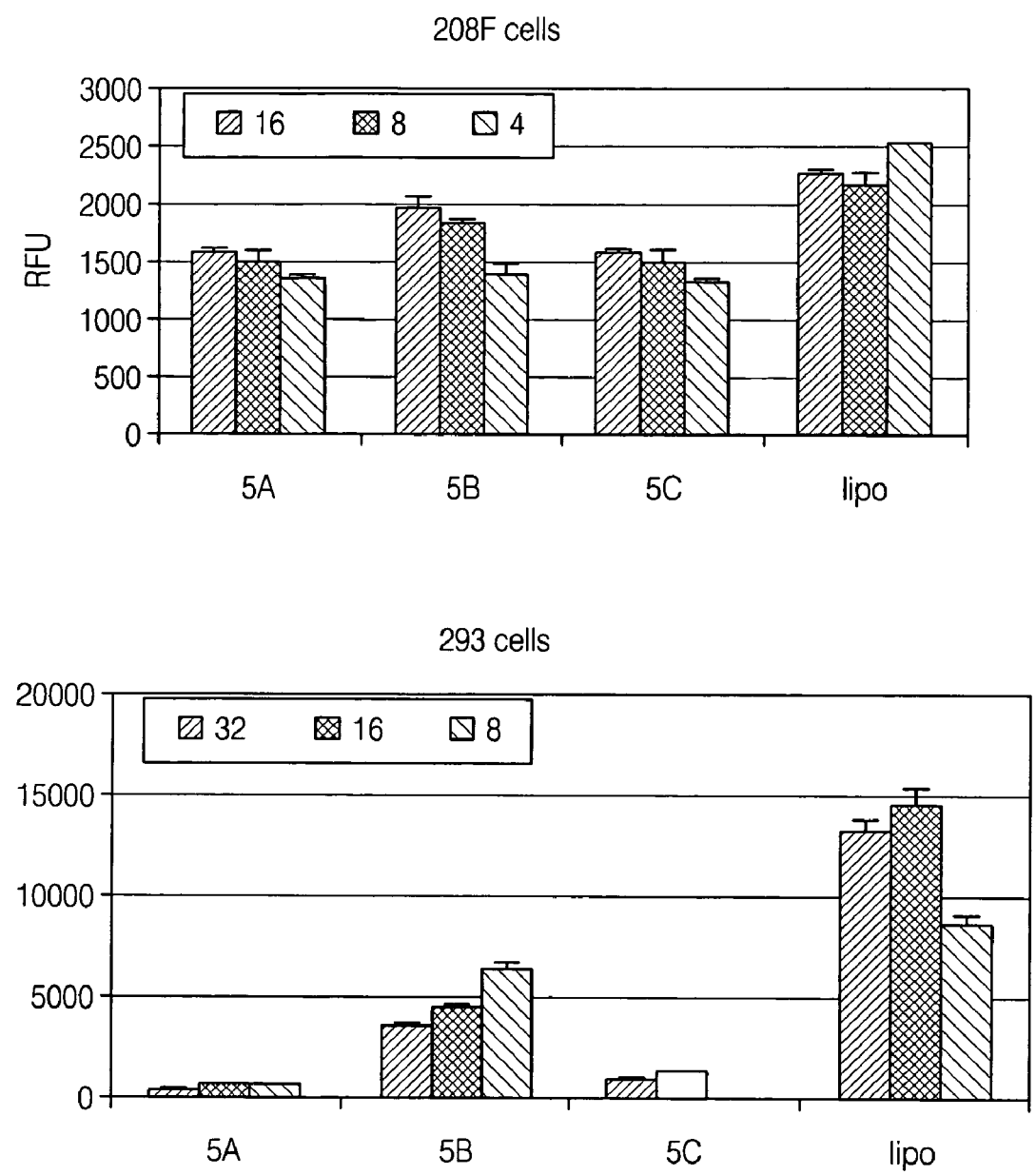
FIG. 3 shows plots of the relative fluorescent level of 208 F and 293 cells after transfection by lipopolymers (5A, 5B and 5C) and lipofectamine 2000 ("lipo").

In order to quantify the transfection efficiency, the relative fluorescent unit of transfected cells was determined by fluorescent microplate reader (FLX 800, Bio-TEK Instruments Co Ltd). The relative fluorescent unit (RFU) of lipofectamine 2000 transfected 293 cells was 14596, about 2.3 times of 5B transfected cells (6318), while the RFU of lipofectamine 2000 and 5C transfected 208F cell was 2544 and 1954 respectively, indicated that in different cells the transfection reagent showed different performance and the new lipopolymers could have better performance in some cell lines (see FIG. 3).

EXAMPLE 9

SiRNA delivery study: SiRNA delivery efficiency was determined in HT1080-EGFP and HeLa EGFP cells, which originated from HT 1080 and HeLa cells respectively with stable EGFP gene expression. The SiRNA targeting EGFP gene and luciferase gene was synthesized by Dharmacon Research Inc. siRNA targeting EGFP and luciferase gene were 21 bp double strand RNA, the sequence of sense strand of them were AAC GAG AAG CGC GAU CAC AUG (SEQ ID NO.: 2) and AAG UGC GCU GCU GGU GCC AAC (SEQ ID NO.: 3 respectively.

1.5×10⁴ HT1080-EGFP and HeLa-EGFP cells were planted in 96-well plate for each well at 24 h before transfection. For each well, an aliquot of 7.5 μl lipopolymer solution at different concentration was added into 7.51 μl DNA solution containing 2.0 pmol siRNA and mixed completely. The DNA and lipopolymer mixture were incubated for 15 min at room temperature to allow for the formation of SiRNA-lipopolymer complexes. The complexes were added to each well and the cells were incubated at 37° C., 5% $CO_2$ for 48 hrs. Lipofectamine were used as positive controls according to the protocol provided by manufacturer. The siRNA delivery efficiency was determined by GFP signal analysis.

Figure 4:
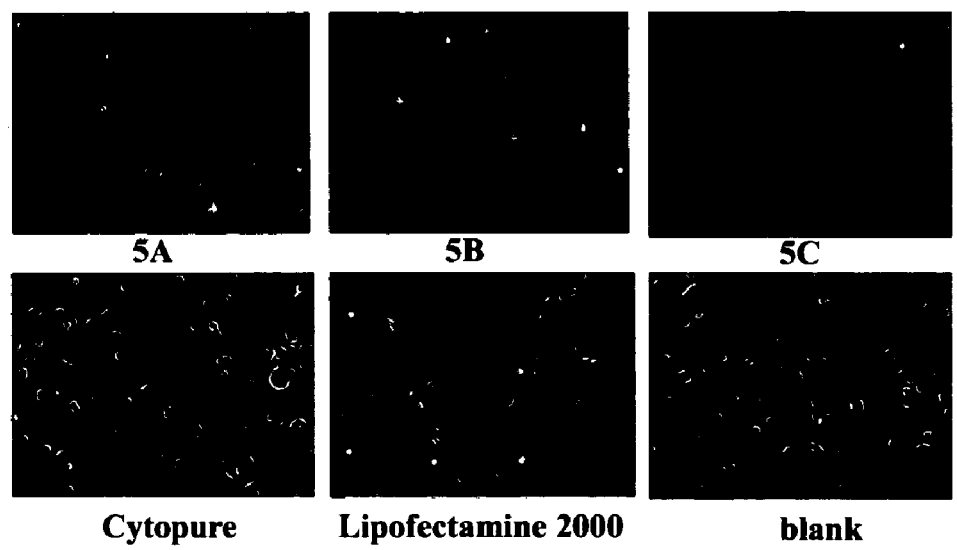
FIG. 4 illustrates typical GFP signals in HT-GFP cells after siRNA delivery by lipopolymers (5A, 5B and 5C) and lipofectamine 2000.
Figure 5:
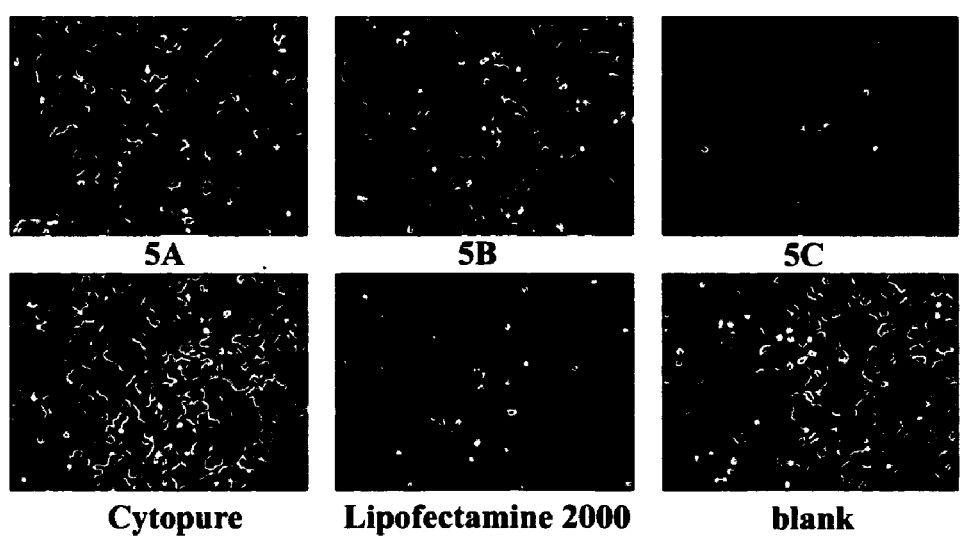
FIG. 5 illustrates typical GFP signal in HeLa-GFP cells after siRNA delivery by lipopolymers (5A, 5B and 5C) and lipofectamine 2000.
Figure 6:
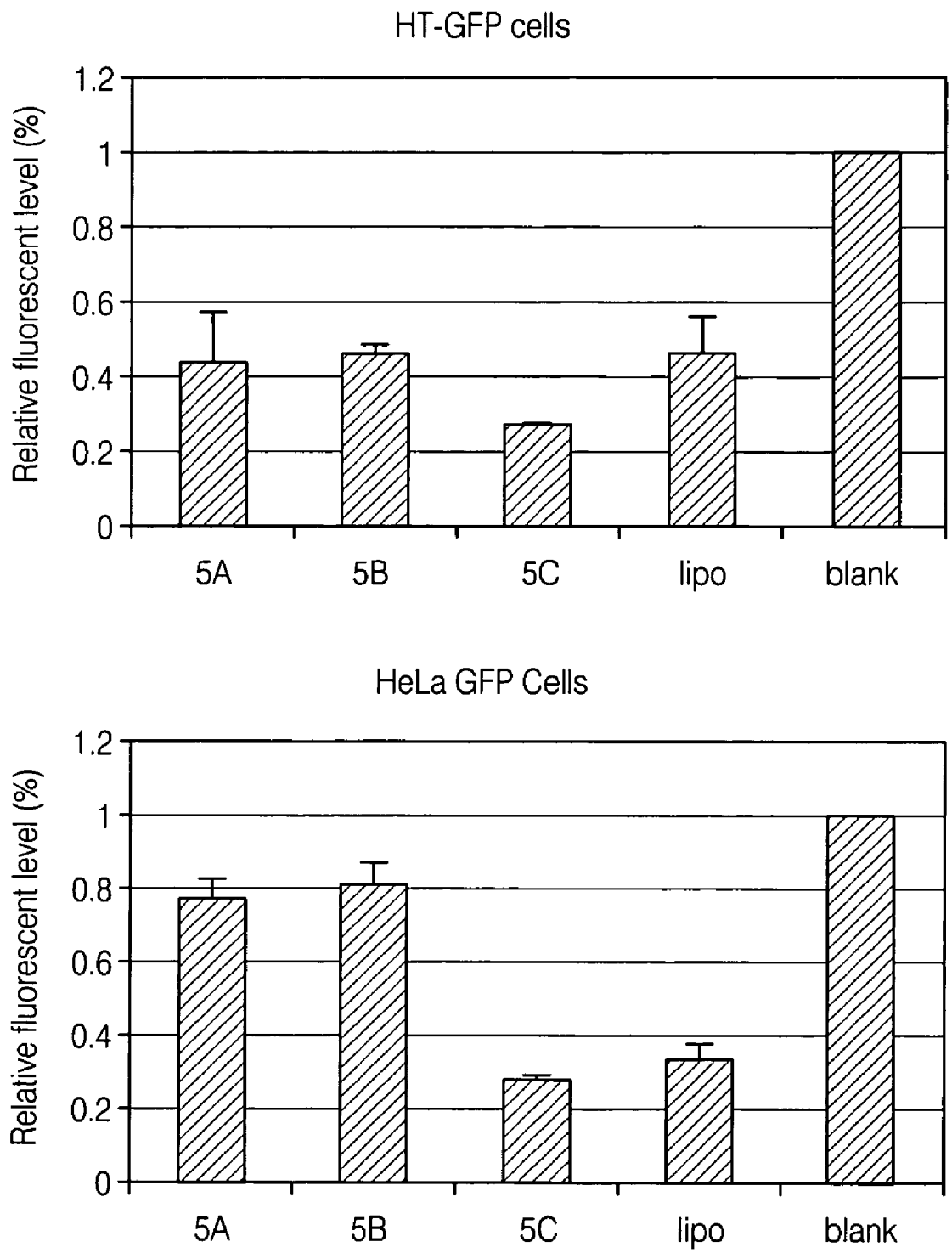
FIG. 6 shows plots of the relative fluorescent level of HT-GFP and HeLa GFP cells siRNA after delivery by lipopolymers (5A, 5B and 5C) and lipofectamine 2000 ("lipo").
Figure 7:
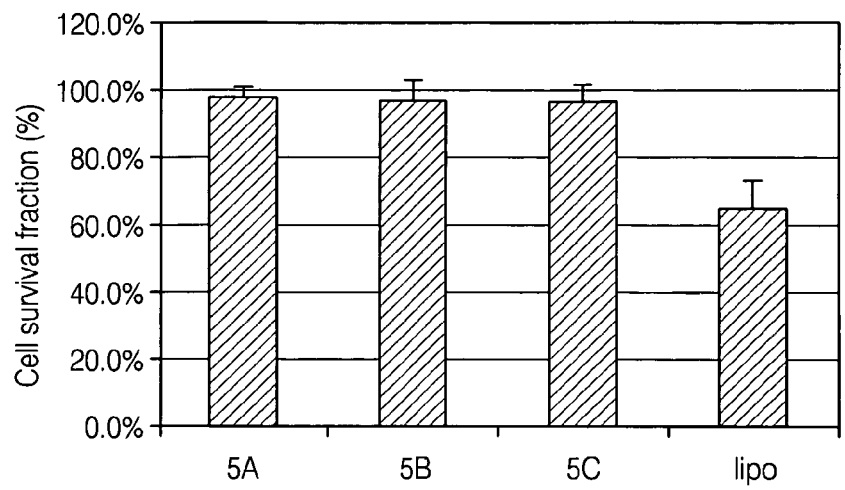
FIG. 7 shows a plot of the cell survival fraction of lipopolymers (5A, 5B and 5C) and lipofectamine 2000 ("lipo") after siRNA delivery.
Figure 8:
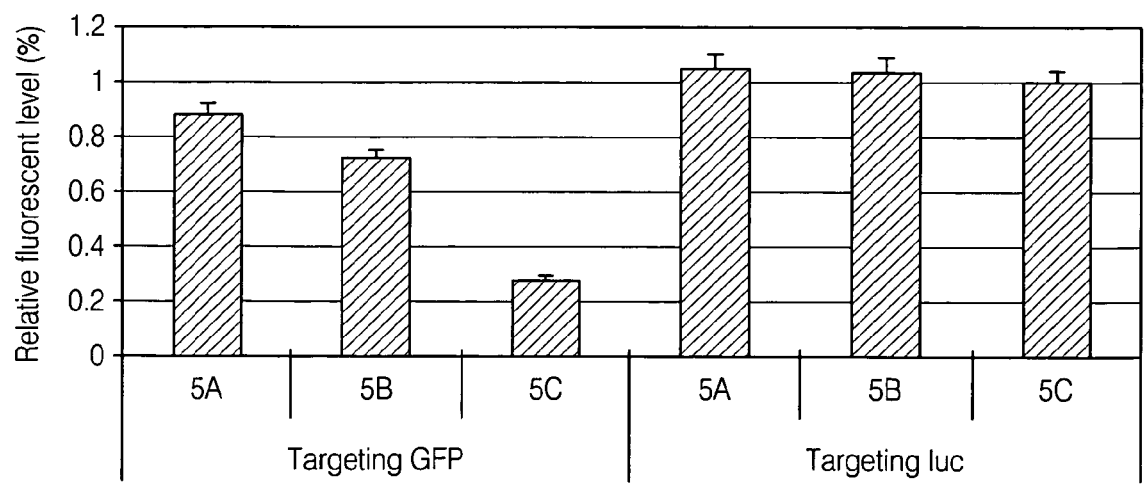
FIG. 8 shows a plot of the relative fluorescent level of HT-GFP gene after different SiRNA delivered by the cationic lipopolymers (5A, 5B and 5C).
Figure 9:
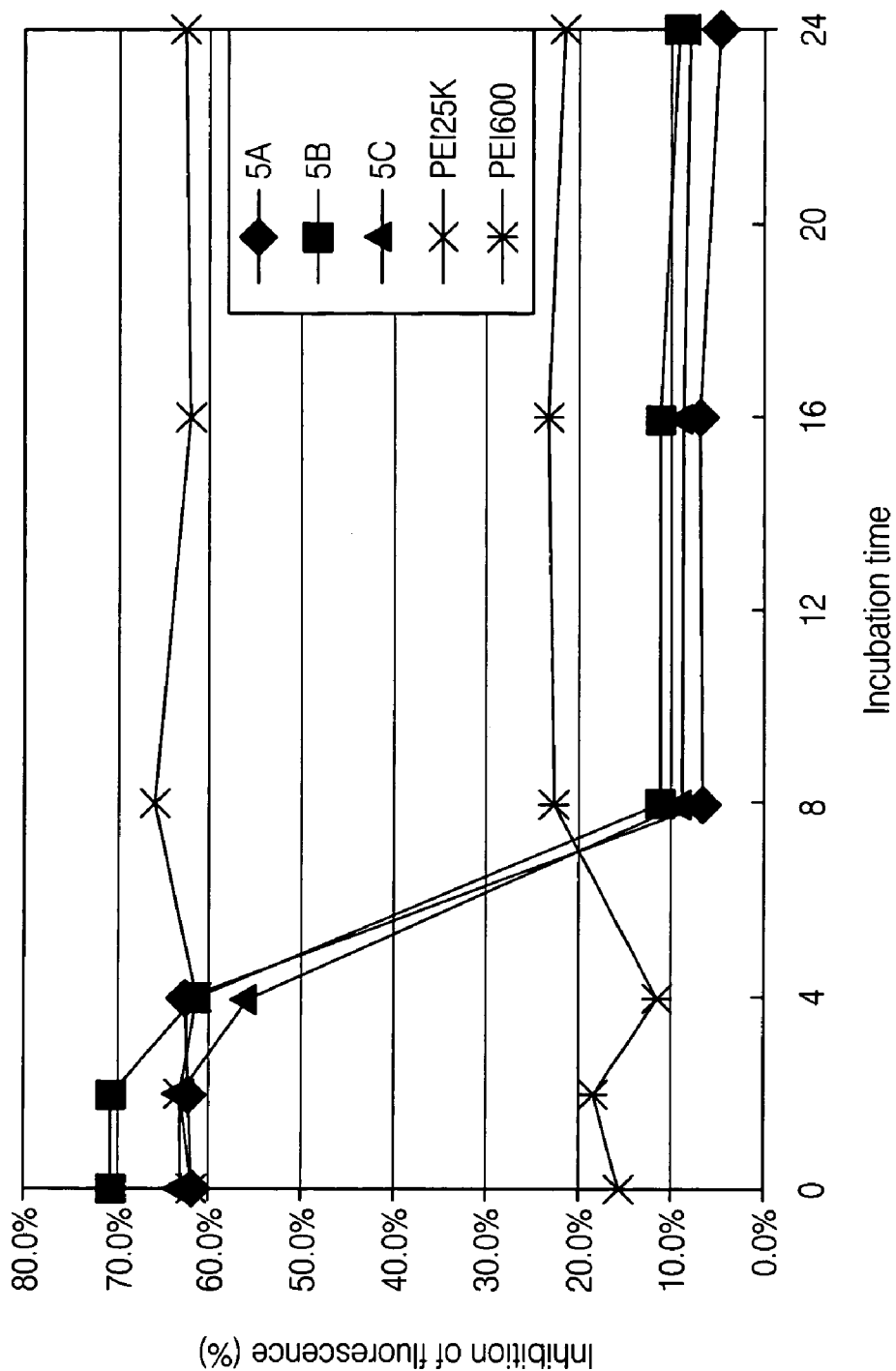
FIG. 9 shows a plot of the relative fluorescent unit of antisense oligo/lipopolymers complexes compared with free oligo solution.

In both HT-GFP and HeLa GFP cells the 5C showed very high siRNA delivery, because the GFP signal was greatly inhibited after 5C mediated siRNA delivery. The GFP signal in 5C mediated siRNA delivered HT-GFP and HeLa-GFP cells was lower than lipofectamine 2000 mediated siRNA delivery cells. The results indicated that 5C had higher SIRNA delivery efficiency than lipofectamine 2000 in both cell lines (FIG. 4 and FIG. 5). On the other hand samples 5A and 5B also showed siRNA delivery efficiency, even though the efficiency was lower than lipofectamine 2000. The relative fluorescent unit was determined by fluorescent microplate reader, and the results showed relative fluorescent level of the 5C mediated siRNA delivery HT1080-EGFP and HeLa EGFP cells only 27-28% of no delivery reagent group, lower than lipofectamine 2000 medicated siRNA delivery cells, which showed about 33 to 46% relative fluorescent level as compare to no delivery reagent group. In other words, the inhibition efficiency of EGFP gene expression in 5C mediated delivered cells was about 72-73%, much higher than lipofectamine 2000, which showed 54-67% of inhibition efficiency. The results indicated that 5C had higher siRNA delivery efficiency than lipofectamine 2000.

EXAMPLE 10

Cytotoxicity Assays: Cytotoxicity of cationic gene carriers was evaluated in mammalian cells using 3-[4,5 dimethylthiazol-2-yl]-2,5-diphenyltetrazolium bromide (MTT). 48 hours after siRNA delivery by the methods described in Example 9, 10 μl of MTT solution (5.0 mg/ml in PBS, Sigma) was added to each well, and incubated at 37° C. for 3 hrs. The medium was then removed and 200 μl DMSO was added into each well to dissolve the formazan crystals produced by living cells. The absorbance of the solution was measured at 570 nm. Cell viabilities was calculated using the equation: Viability (%)={$AbS_{570\ (sample)}/Abs_{570\ control}$}. The control indicated no any reagent or siRNA was added into cells. The results showed that the cytotoxicity of all 3 samples, 5A, 5B, and 5C, were very low, higher than 95% cell survival after siRNA delivery at optimal condition, while the cell viability was about 65% after siRNA delivery by lipofectamine 2000. Because HeLa cells were sensitive to the cytotoxicity of transfection reagent, the results suggested that the new lipopolymers had very low cytotoxicity.

EXAMPLE 11

Specificity of lipopolymers in siRNA delivery: To evaluate whether inhibition of GFP signal was caused by cytotoxicity or other non-specific factors, the specificity of siRNA delivery was studied. The SiRNA targeting GFP and Luc gene were delivered into HT-GFP cells by 5A, 5B and 5C. The GFP signal was observed at 48 hrs after delivery. It was found that the 5B and 5A had low delivery efficiency, because there was not any change in GFP signal. 5C showed very high delivery efficiency, because 72% of GFP was inhibited at 48 hrs after SiRNA delivery (targeting GFP gene) when at optimal condition. On the other hand, when SiRNA targeting luc gene was used, not any inhibition was found. The results indicated the GFP signal was specifically inhibited by SiRNA delivery, instead of cytotoxicity caused inhibition.

EXAMPLE 12

Degradation study: In order to detect biodegradation, the lipopolymers were diluted at opti MEM to final concentration of 320 μg/ml and incubated at 37° C. for 2, 4, 8, 24 hours respectively. The DNA binding affinities of samples were determined by FITC-labeled antisense oligo. 100 μl polymers were added into 100 μl oligo solution (2 μmol/L) in 96 well plate while vortexing and the mixture was incubated for 15 min. After that, the fluorescent was determined by fluorescent microplate reader (sensitivity=45). The relative fluorescent unit of free oligo solution (the oligo solution only mixed with 100 μl opti MEM solution) was about 5200 RFU, and PEI25K or PEI 600 was 1823 and 4350 respectively. The results indicated that PEI 25K with high DNA binding affinity showed high inhibition on fluorescent (about 64% inhibition), while PEI 600 showed very inhibition on fluorescent unit (18%), because PEI 600 usually showed very low DNA binding affinity. As for the cationic lipid based polymers, the inhibition efficiency on fluorescent was about 65% to 70%, indicating the polymers had high DNA binding affinity.

After incubation at 37° C. in opti MEM for 24 h, both PEI 25K and PEI600 showed no significant change in DNA binding affinity, because almost no change was found in fluorescent signal as compare to original samples, indicated that PEI 25K was not degradable. However, after being incubated at 37° C. for 8 h, the inhibition efficiency of 5A, 5B and 5C on fluorescent was gradually reduced to about 10%, lower then PEI 600. The results indicated that the lipopolymers were degradable in opti MEM.

EXAMPLE 13

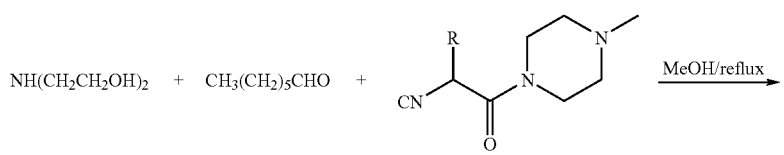

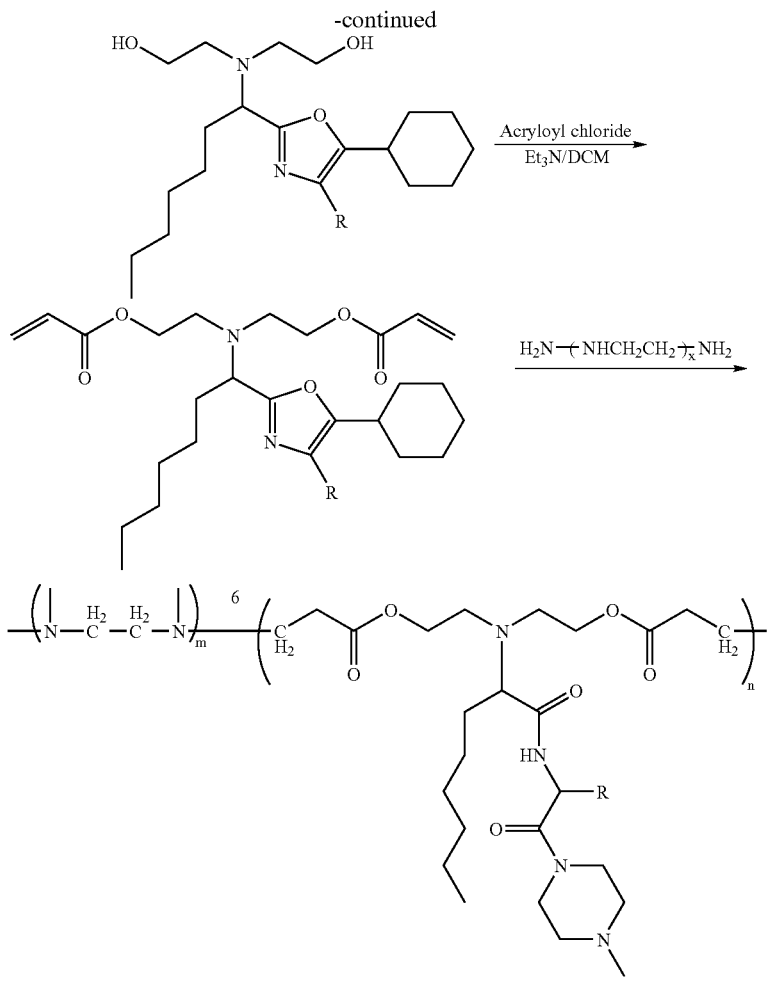

Pentaethylenehexamine (PEHA) (43 mg, 0.19 mmol) (Aldrich) was weighed and placed in a small vial, and 2 ml of ethanol was added. After the PEHA completely dissolved, compound 6 (n×100 mg, n×0.19 mmol) was quickly added into the PEHA solution while stirring. The reaction mixture was stirred for 2 hours at room temperature (25° C.). Then, the reaction mixture was neutralized by adding 1 ml of 4M HCl in ether. The white precipitate was filtered, washed with ethanol, and dried at room temperature under reduced pressure. The obtained polymer 7 was characterized by NMR and agarose gel electrophoresis.

Other crosslinked, degradable cationic lipopolymers were prepared in a similar manner by varying the ratio of PEHA to 6 as follows: 7A: PEHA/6=1/1; 7B: PEHA/6=2/1; 7C: PEHA/6=3/1; 7D: PEHA/6=4/1; 7E: PEHA/6=5/1; and 7F: PEHA/6 =6/1.

EXAMPLE 14

Cell culture: HEK 293 cells and HeLa 705 cells were maintained in DMEM medium containing 10% FBS, 100 units/ml penicillin and 100 μg/ml streptomycin at 37° C., 5% $CO_2$ and 100% humidity conditions. CHO-AA8 luc was cultured in MEM medium containing 10% FBS and antibiotics, other condition are the same as 293 and HeLa 705 cells. The cells have a doubling time of about 20 hours and were split every 3-4 days to avoid confluency.

Plasmid DNA preparation: pEGFP-N1 plasmid, purchased from BD Sciences Clontech company, encodes a red-shifted variant of wild-type GFP which has been optimized for brighter fluorescence and higher expression in mammalian cells. The GFP protein was controlled by immediate early promoter of CMV ($P_{CMV\,IE}$). pCMV-luc plasmid was constructed in same way. The plasmids were amplified in DH5α *E. coli* and purified with Qiagen Plasmid Max Preparation Kit, and had an A260/A280 greater than 1.7.

Figure 10:
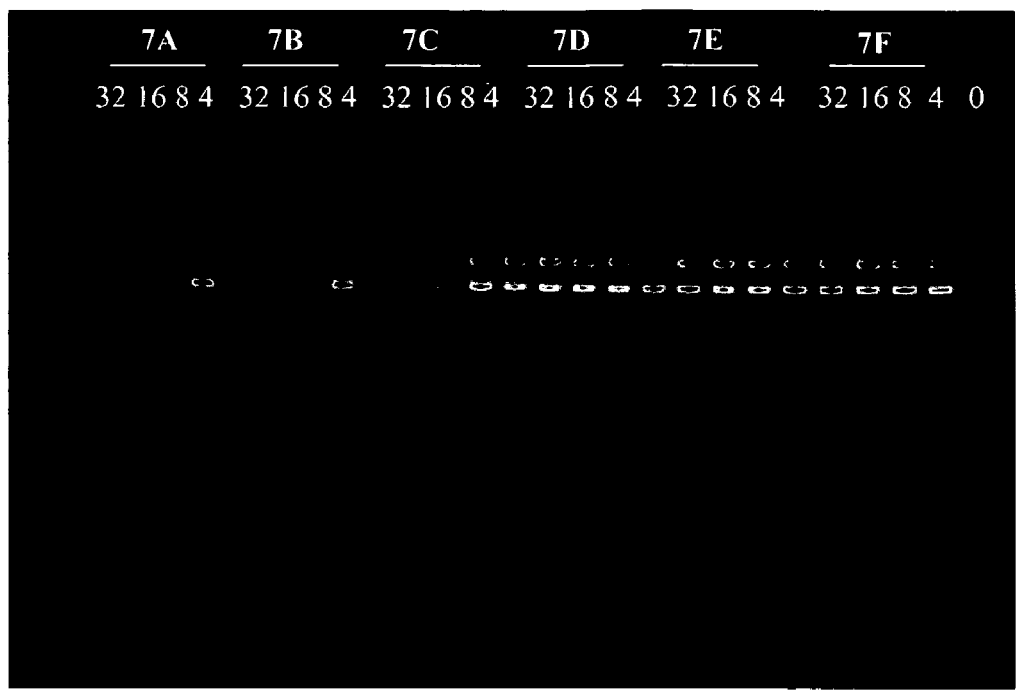
FIG. 10 illustrates gel electrophoresis results for binding of polymer 6 to DNA.

DNA binding of polymer 7: A series of samples of polymer 7 and DNA were diluted separately in opti MEM, then 10 μl polymer 7 solution was added into the DNA solution (20 μg/ml) while vortexing. The polymer/DNA ratios were 32:1, 16:1, 8:1 and 10:1. The mixtures were incubated at room temperature for 15 min to form polymer/DNA complexes. After that, 5 μl DNA loading buffer was added into the complexes and 15 μl of mixture was added into 0.3% agarose gel for each well. The sample was subjected to electrophoresis at 100V for about 30 min and the gel was visualized with UV light. The results of DNA binding affinity are shown in FIG. 10. Most samples showed lower DNA binding affinity. For examples, even when polymer/DNA ratio was 32:1, the DNA electrophoresis pattern of 7B, 7C, 7D, 7E and 7F/DNA mixture was same as free DNA (polymer amount was 0). However, when polymer/DNA ratio was 32:1 and 16:1, the plasmid was retarded by 7A, indicating sample 7A had DNA binding affinity.

EXAMPLE 15

In vitro gene transfection: 293 cells were plated in 96-well tissue culture plates ($5 \times 10^4$ cells/well) and incubated overnight in DMEM with 10% FBS. For each well, an aliquot of 7.5 µl lipopolymer 7 solution at different concentration was added into 7.5 µl DNA solution containing 0.6 µg of pEGFP-N1 plasmid and mixed completely. The DNA and lipopolymer 7 mixtures were incubated for 15 min at room temperature to allow for the formation of DNA-lipopolymer complexes. The complexes were added to each well and the cells were incubated at 37° C., 5% $CO_2$ for 24 hrs. The EGFP gene transfection efficiency was determined by GFP signal analysis. Lipofectamine were used as positive controls according to the protocol provided by manufacturer. Green fluorescent signal in transfected cells from samples were observed under fluorescent microscope (Olympus, filter 520 nm). Cells were photographed using a 10× objective. The percent of cells with GFP signal in transfected cultures was determined from counts of three fields for optimal cationic polymer amounts.

Figure 11:
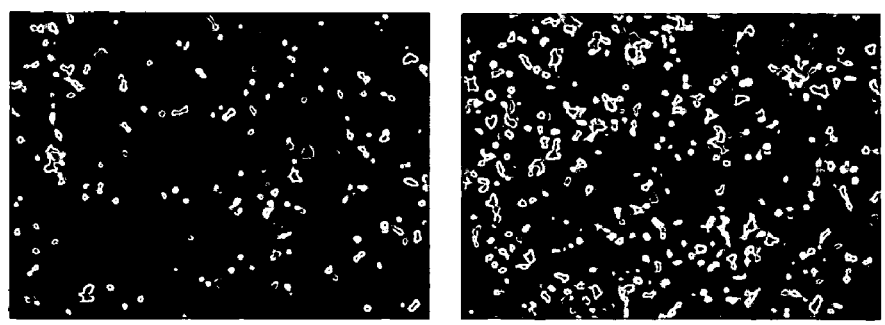
FIG. 11 illustrates typical GFP signals of 293 cells after transfection by 7A and lipofectamine 2000.

About 24 h after transfection, about 28% of 7A transfected 293 cells showed transfection efficiency. The result indicated that lipoploymer 7A is a transfection reagent (FIG. 11).

EXAMPLE 16

Antisense oligo delivery: Dr. Kole in University of Northern Carolina developed luciferase 705 gene system for functional assay of antisense delivery. In this system, human β-globin with mutation at 705 was inserted into the sequence between luciferase cDNA. This plasmid was introduced into HeLa cell for stable gene expression, the cell line was termed as HeLa luc705. Usually the cells exhibit low luciferase activity, because it expresses the wrong luciferase protein. However, antisense oligo binding to 705 sequences will block the wrong splicing site and produce luciferase protein with biological activity. Luciferase 705 is now used as functional model in antisense oligo delivery: higher luciferase activity indicates higher efficiency of antisense delivery.

Antisense oligo delivery efficiency of polymer 7 samples was evaluated in Luc 705 cell line. The final concentration of oligo targeting luc 705 was 1.0 µmol/L, the concentration of polymers was 320 and 160 µg/ml (same as the amount of polymers when polymer/DNA ratio was 16: and 8:1 during transfection. The luciferase activity was determined) about 24 h after transfection.

Figure 12:
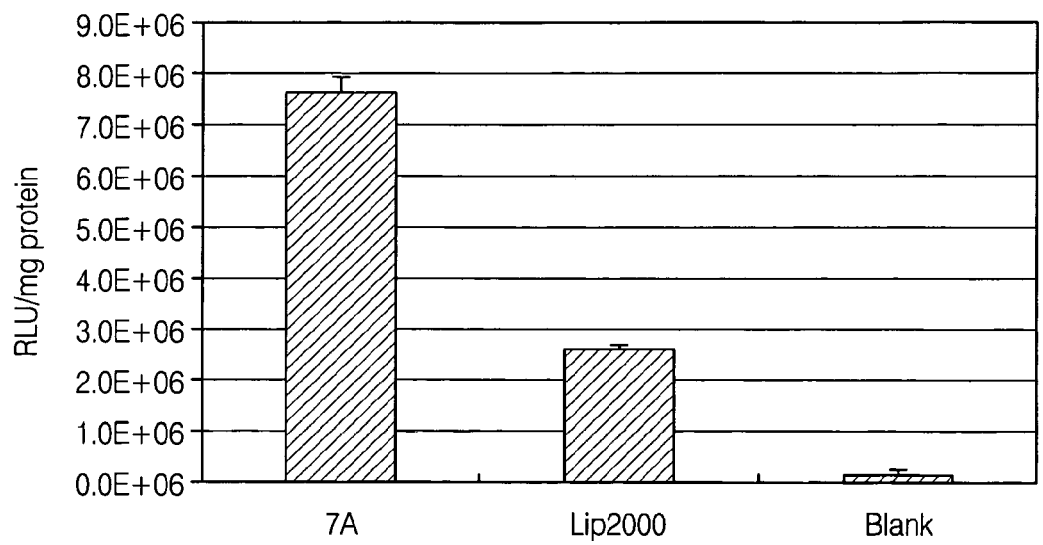
FIG. 12 shows a plot of Luciferase activity in luc 705 cell after antisense oligo delivery by polymer 7A and by lipofectamine 2000.

The background luciferase activity in 705 cell was about $1.6 \times 10^5$ RLU/mg protein. The luciferase activity of antisense oligo delivered to the cell by 7A was greatly increased, near 50 times that in the non-delivered cells. The delivery efficiency of lipofectamine 2000 was less, about 15 times that in the non-delivered cells. The results indicated that lipid-polymer 7A has higher antisense oligo delivery efficiency than lipofectamine 2000 (FIG. 12).

EXAMPLE 17

The SiRNA delivery efficiency of lipo-polymers was determined in CHO-AA8-luc cell line. CHO-AA8 Luc is Tet-off cell lines, in which luciferase gene expression was controlled by Dox. The luciferase gene expression will be shut down, when Dox is added into cell, and it will express after Dox is removed.

In SiRNA delivery study, the existing protein of a target gene may affect the evaluation, because if the half-life time is long, the protein may be detected, even though the target gene was already shut down. In this case, CHO-AA8 Luc cell showed advantages. The luciferase gene expression could be shut down by adding Dox to reduce background protein. During SiRNA delivery, the Dox could be removed by changing the medium, and the luciferase gene began to express, at same time, if the SiRNA was successfully delivered into the cell, the luciferase expression level could be inhibited by SiRNA.

The CHO AA8 luc was seeded in 96 well plate with Dox. 18-24 h later, the SiRNA cassette/polymer 7 complexes were made. The final concentration of polymers was 320 and 160 µg/ml (same concentration as that 16:1 and 8:1 in gene transfection). The amount of SiRNA cassette was 150 ng/ml. After medium change and the cell washed with PBS, the SiRNA/polymer 7 complexes were added into cell. After cell was incubated at 37° C. for 48 h, luciferase activity was detected.

Figure 13:
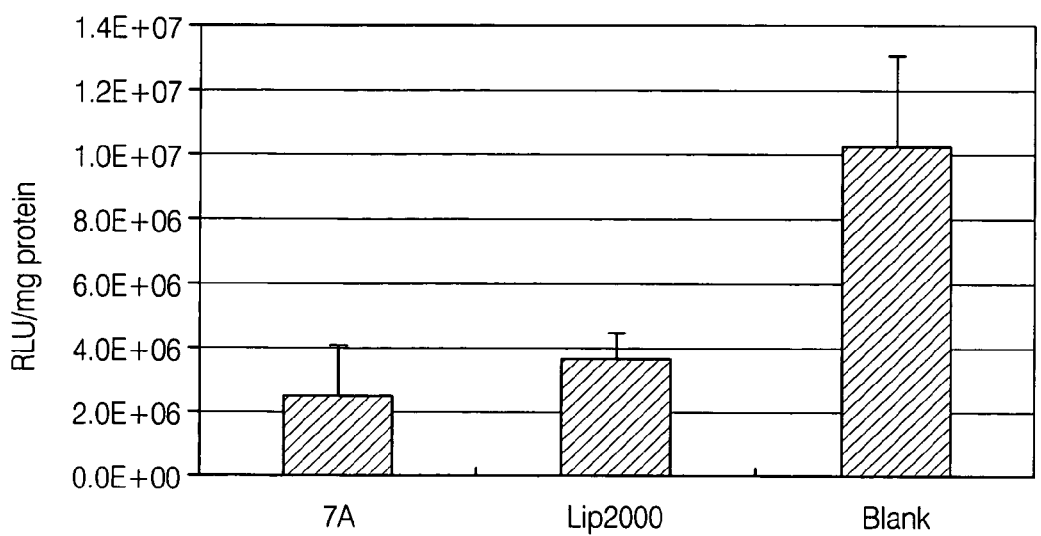
FIG. 13 shows a plot of Luciferase activity in CHO-AA8 luc after polymer 7A and lipofectamine 2000 mediated SiRNA delivery.

The luciferase activity of control (blank) was about $10^7$ RLU/mg protein, after SiRNA cassette delivery by 7A and lipofectamine 2000, the luciferase activity was greatly inhibited to 2.47 and $3.49 \times 10^6$ RLU/mg protein respectively. The results indicated 7A could efficiently delivery siRNA cassette into cells and the delivery efficiency was higher than lipofectamine (FIG. 13).

EXAMPLE 18

Figure 14:
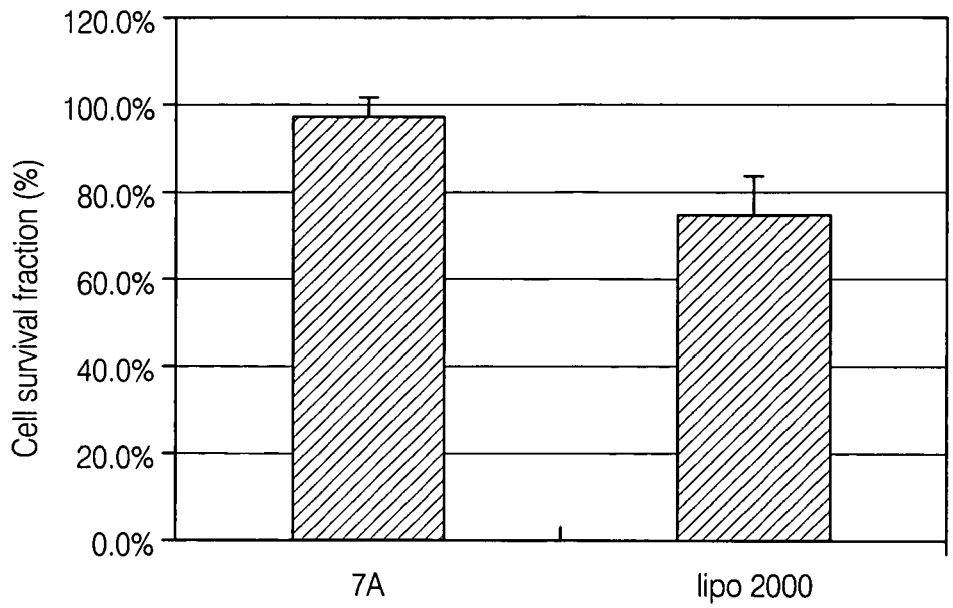
FIG. 14 shows a plot illustrating cell survival fraction after transfection using 7A and lipofectamine.

Cytotoxicity of cationic lipolymer 7 gene carriers were evaluated in mammalian cells using 3-[4,5 dimethylthiazol-2-yl]-2,5-diphenyltetrazolium bromide (MTT). 48 h after gene transfection by the methods described above, 10 µl of MTT solution (5.0 mg/ml in PBS, Sigma) was added to each well, and incubated at 37° C. for 3 hours. The medium was then removed and 200 µl DMSO was added into each well to dissolve the formazan crystals produced by living cells. The absorbance of the solution was measured at 570 nm. Cell viabilities was calculated using the equation: Viability (%)={$Abs_{570\ (sample)}$/$Abs_{570\ control}$}. The results showed that the cytotoxicity of 7A was very low, more than 95% cell survival after siRNA delivery at optimal condition, while the cell viability was about 75% after siRNA delivery by lipofectamine 2000. The results indicated 7A has very lower cytotoxicity (FIG. 14).

EXAMPLE 19

Biodegradation of polymer 7: Polymer 7A was diluted with opti MEM to a final concentration 320 µl/ml. A series of samples were incubated at 37° C. for 4 hours, 8 hours and 24 hours, then samples were taken for gene transfection study in 293 cell seed in 96 well plate. The transfection was performed by the protocol described above. The GFP signal was observed at 24 hours after transfection.

Figure 15:
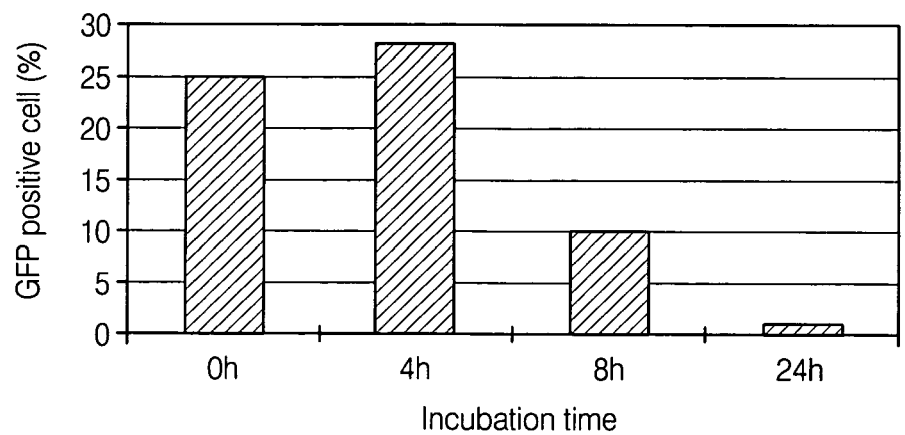
FIG. 15 shows a plot of GFP transfection efficiency of 7A after incubation in opti MEM for various periods of time.

The GFP gene transfection efficiency of 7A was about 25%, and there was no significant change in transfection efficiency after the samples was incubated for 4 hours. The transfection efficiency was greatly reduced after the sample was incubated for 8 h, and almost no transfection efficiency was found after the sample was incubated for 24 hours. The results indicated that the 7A was biodegradable under neutral conditions (FIG. 15).

It will be appreciated by those skilled in the art that various omissions, additions and modifications may be made to the compositions and methods described above without departing from the scope of the invention, and all such modifications and changes are intended to fall within the scope of the invention, as defined by the appended claims.

What is claimed is:

1. A polymer comprising a recurring unit selected from the group consisting of formula (Ia) and formula (Ib):

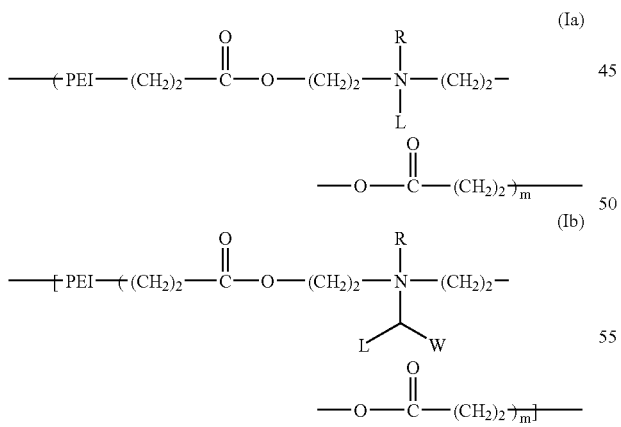

wherein:

PEI is a polyethyleneimine recurring unit;

R is selected from the group consisting of an electron pair, hydrogen, $C_2$-$C_{10}$ alkyl, $C_2$-$C_{10}$ heteroalkyl, $C_5$-$C_{30}$ aryl, and $C_2$-$C_{30}$ heteroaryl;

L is selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{50}$ aryl; $C_2$-$C_{50}$ heteroaryl; $C_2$-$C_{50}$ alkynyl, $C_2$-$C_{50}$ heteroalkynyl, $C_5$-$C_{50}$ aryl; $C_2$-$C_{50}$ heteroaryl; $C_2$-$C_{50}$ carboxyalkenyl, $C_2$-$C_{50}$ carboxyheteroalkenyl; $C_{12}$ to $C_{18}$ fatty acid, cholesterol, a $C_{12}$ to $C_{18}$ fatty acid derivative and a cholesterol derivative;

W is a cationic moiety comprising from about 2 to about 50 carbon atoms; and m is an integer in the range of about 1 to about 30.

2. The polymer of claim 1 in which the PEI is represented by a recurring unit of formula (II)

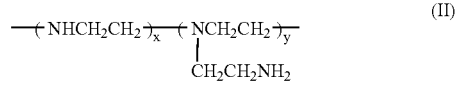

wherein x is an integer in the range of about 1 to about 100 and y is an integer in the range of about 1 to about 100.

3. The polymer of claim 1 in which the polymer comprises a recurring unit of the formula (Ia).

4. The polymer of claim 1 in which the polymer comprises a recurring unit of the formula (Ib).

5. The polymer of claim 1 in which W comprises an amine and a carbon-containing group selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{50}$ aryl; $C_2$-$C_{50}$ heteroaryl; $C_2$-$C_{50}$ carboxyalkenyl, and $C_2$-$C_{50}$ carboxyheteroalkenyl.

6. The polymer of claim 1 that is biodegradable.

7. The polymer of claim 1 that is degradable by a mechanism selected from the group consisting of hydrolysis, enzyme cleavage, reduction, photo-cleavage, and sonication.

8. The polymer of claim 1 in which L is selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_2$-$C_{50}$ alkynyl, $C_2$-$C_{50}$ heteroalkynyl, $C_2$-$C_{50}$ carboxyalkenyl, and $C_2$-$C_{50}$ carboxyheteroalkenyl.

9. The polymer of claim 1 in which L is selected from the group consisting of $C_{12}$ to $C_{18}$ fatty acid, cholesterol, a $C_{12}$-$C_{18}$ fatty acid derivative and a cholesterol derivative.

10. The polymer of claim 1 in which the polyethyleneimine recurring unit has a molecular weight in the range of about 600 Daltons to about 25,000 Daltons.

11. The polymer of claim 1 having a weight average molecular weight in the range of about 500 Daltons to about 1,000,000 Daltons.

12. The polymer of claim 1 having a weight average molecular weight in the range of about 2,000 Daltons to about 200,000 Daltons.

13. The polymer of claim 1 which is crosslinked.

14. A composition comprising a biomolecule complexed to the polymer of claim 1.

15. The composition of claim 14 in which the biomolecule is selected from the group consisting of nucleic acid, protein, peptide, lipid, and carbohydrate.

16. The composition of claim 15 in which the nucleic acid is selected from the group consisting of DNA, single strand RNA, double strand RNA, ribozyme, DNA-RNA hybridizer, and antisense DNA.

17. The composition of claim 15 in which the nucleic acid is siRNA or antisense oligo.

18. The composition of claim 14 further comprising a delivery enhancing agent capable of entering a eukaryotic cell.

19. The composition of claim 18 further comprising a diagnostic imaging composition that is complexed to the polymer.

20. The composition of claim 18 in which the delivery enhancing agent facilitates one or more functions in the eukaryotic cell selected from the group consisting of receptor recognition, internalization, escape of the biomolecule from a cell endosome, nucleus localization, and biomolecule release.

21. The composition of claim 20 in which the biomolecule is selected from the group consisting of nucleic acid, peptide, protein, and carbohydrate.

22. The composition of claim 18 in which the delivery enhancing agent is coupled to the polymer.

23. A method of delivering a biomolecule to a eukaryotic cell comprising contacting the cell with the composition of claim 14 to thereby deliver the biomolecule to the cell.

24. A method of administering a nucleic acid to a mammal comprising locally administering the composition of claim 17 to a cell of said mammal.

25. A composition comprising a diagnostic imaging agent that is complexed to the polymer of claim 1.

26. A method of delivering a diagnostic imaging agent to a mammal, comprising administering the composition of claim 25 to the mammal.

27. A polymer library comprising a plurality of polymers of claim 1, wherein at least one parameter selected from the group consisting of R, L, PEI, W, and m is different for at least two of the polymers.

28. A medical diagnostic system comprising the polymer of claim 1 and a ligand that recognizes a specific receptor of a eukaryotic cell.

29. The medical diagnostic system of claim 28 in which the polymer is coupled to the ligand.

30. A pharmaceutical composition comprising a sensitizer agent and the polymer of claim 1.

31. The pharmaceutical composition of claim 30 in which the sensitizer agent is sensitive to visible radiation, ultraviolet radiation, or both.

32. The pharmaceutical composition of claim 30 in which the polymer has an affinity for a biomolecule.

33. A diagnostic imaging composition comprising an image contrast agent and the polymer of claim 1.

34. The diagnostic imaging composition of claim 33 further comprising a targeting agent.

35. The compound of claim 1, wherein the polymer comprises the recurring unit of formula (Ia) in which PEI is a polyethyleneimine recurring unit; R is an electron pair or hydrogen; L is a $C_2$-$C_{50}$ carboxyalkenyl; and m is an integer in the range of about 1 to about 30.

* * * * *

SEQUENCE LISTING

```
<160> NUMBER OF SEQ ID NOS: 3

<210> SEQ ID NO 1
<211> LENGTH: 7
<212> TYPE: PRT
<213> ORGANISM: Simian Virus 40

<400> SEQUENCE: 1

Pro Lys Lys Lys Arg Lys Val
 1               5

<210> SEQ ID NO 2
<211> LENGTH: 21
<212> TYPE: RNA
<213> ORGANISM: Artificial Sequence
<220> FEATURE:
<223> OTHER INFORMATION: Synthetically prepared ribonucleic acid
      sequence

<400> SEQUENCE: 2
aacgagaagc gcgaucacau g                                             21

<210> SEQ ID NO 3
<211> LENGTH: 21
<212> TYPE: RNA
<213> ORGANISM: Artificial Sequence
<220> FEATURE:
<223> OTHER INFORMATION: Synthetically prepared ribonucleic acid
      sequence

<400> SEQUENCE: 3
aagugcgcug cuggugccaa c                                             21
```